(12) United States Patent  (10) Patent No.: US 8,409,171 B2
Hannon et al.  (45) Date of Patent: Apr. 2, 2013

(54) FLUID DRAINAGE CATHETER HAVING AN EXTERNAL FLOW PATH

(75) Inventors: David Hannon, Mayo County (IE); George J. Cisko, Jr., Spring Grove, IL (US)

(73) Assignee: Hollister Incorporated, Libertyville, IL (US)

( * ) Notice: Subject to any disclaimer, the term of this patent is extended or adjusted under 35 U.S.C. 154(b) by 845 days.

(21) Appl. No.: 12/336,818

(22) Filed: Dec. 17, 2008

(65) Prior Publication Data

US 2009/0221992 A1    Sep. 3, 2009

Related U.S. Application Data

(60) Provisional application No. 61/032,253, filed on Feb. 28, 2008.

(51) Int. Cl.
*A61M 27/00* (2006.01)

(52) U.S. Cl. ..................... 604/544; 604/93.01

(58) Field of Classification Search ............ 604/93.01, 604/317, 540–544
See application file for complete search history.

(56) References Cited

U.S. PATENT DOCUMENTS

| | | |
|---|---|---|
| 2,460,473 A | 2/1949 | Larkin et al. |
| 3,769,981 A | 11/1973 | McWhorter |
| 3,815,608 A | 6/1974 | Spinosa et al. |
| 3,981,297 A | 9/1976 | Dunn et al. |
| 4,210,478 A * | 7/1980 | Shoney .................. 156/242 |
| 4,307,723 A | 12/1981 | Finney |
| 4,652,258 A | 3/1987 | Drach |
| 4,787,892 A | 11/1988 | Rosenberg |
| 5,250,029 A | 10/1993 | Lin et al. |
| 5,300,022 A | 4/1994 | Klapper et al. |
| 5,562,622 A | 10/1996 | Tihon |
| 5,628,770 A | 5/1997 | Thome et al. |
| 5,738,654 A | 4/1998 | Tihon |
| 5,769,818 A | 6/1998 | El Maoued |
| 5,853,518 A | 12/1998 | Utas |
| 6,409,717 B1 | 6/2002 | Israelsson et al. |

(Continued)

FOREIGN PATENT DOCUMENTS

| | | |
|---|---|---|
| EP | 0299622 | 1/1989 |
| EP | 0 795 339 B1 | 11/2002 |

(Continued)

OTHER PUBLICATIONS

English translation of FR 2,240,026 to Rhone-Poulenc Chemical Factories, 1975.*

(Continued)

*Primary Examiner* — Melanie Hand
(74) *Attorney, Agent, or Firm* — Cook Alex Ltd.

(57) ABSTRACT

A fluid drainage catheter comprises a catheter tube having a proximal and a distal end and a cylindrical wall with a lumen extending generally from the proximal to the distal end to permit the passage of fluid therethrough. The catheter tube is formed such that the proximal end has a closed tip for insertion of the catheter tube into a body cavity and the distal end has an opening for the drainage of from the body cavity through the lumen of the catheter tube. The cylindrical wall has an outer surface with at least one defined external flow path extending generally in a longitudinal direction from a point in proximity to the closed tip to a point distally thereof. With this arrangement, at least one drainage eye is associated with the defined external flow path and extends completely through the catheter tube from the outer surface to the lumen to permit fluid in the flow path to pass through the drainage eye into the lumen.

26 Claims, 9 Drawing Sheets

U.S. PATENT DOCUMENTS

| | | |
|---|---|---|
| 6,743,198 B1 | 6/2004 | Tihon |
| 7,087,048 B2 | 8/2006 | Israelsson et al. |
| 2003/0018293 A1 | 1/2003 | Tanghoj et al. |

FOREIGN PATENT DOCUMENTS

| | | |
|---|---|---|
| FR | 2240026 A1 | 3/1975 |
| GB | 2284764 | 6/1995 |
| WO | WO 2004/056290 | 7/2004 |
| WO | WO 2007/005734 | 1/2007 |
| WO | WO 2009/052838 | 4/2009 |

OTHER PUBLICATIONS

International Search Report for corresponding International Application No. PCT/US2008/087124 (Jun. 22, 2009).

Written Opinion of the International Searching Authority for corresponding International Application No. PCT/US2008/087124 (Jun. 22, 2009).

* cited by examiner

FLUID DRAINAGE CATHETER HAVING AN EXTERNAL FLOW PATH

FIELD OF THE DISCLOSURE

The present disclosure is generally related to catheters for the drainage of fluid from the body, and in one particular application, to urinary catheters for draining urine from the bladder.

BACKGROUND OF THE DISCLOSURE

It is generally well known that catheterization can be an important adjunct to healthcare in many instances. This is known to be the case for draining fluid from a cavity in a body and is particularly the case in connection with urinary catheters which serve to drain urine from the bladder. The regular drainage of the bladder is well recognized as an important function for urological health.

For those suffering from abnormalities of the urinary system, intermittent catheterization has been found to be a good option. Those with such abnormalities often find it desirable to use individually packaged, sterile catheters on a regular basis for drainage of urine from the bladder. Among the more important criteria for intermittent catheters is that they provide complete drainage of the bladder.

Similarly, indwelling catheterization is known to be a good option for many patients who are substantially bedridden. Patients who are hospitalized for extended periods of time as well as others who are rendered immobile for various reasons often benefit from the use of Foley catheters. Typically, Foley catheters are recommended by healthcare providers to remain in place for a period of up to around thirty days.

As with intermittent catheters, it is important that Foley catheters ensure substantially complete drainage of the bladder to maintain good urological health.

Unfortunately, minimizing residual urine in the bladder depends on substantially accurate positioning of an intermittent catheter which is oftentimes difficult to ensure. In particular, the lower eye of the intermittent catheter must be accurately positioned with respect to the internal neck of the bladder in order to be relatively certain of removing the maximum amount of urine. Additionally, however, the soft tissue in the neck area of the bladder sometimes has a tendency to get sucked into the eye, making it difficult to completely drain the bladder.

As a result, intermittent catheters present both a positioning/withdrawing challenge and also an eye blocking problem causing difficulty in ensuring substantially complete bladder drainage.

With regard to Foley catheters, an encrustation problem results from a crystalline buildup which usually begins on the catheter eyes and extends into the lumen of the catheter just below the eyes. In this connection, it is known that encrustation can lead to complete blocking of the Foley catheter requiring a catheter change well before the recommended time.

As a result, there are problems with both intermittent catheters and Foley catheters which relate to their ability to ensure complete bladder drainage thereby causing them to be less than fully effective in ensuring good urological health.

SUMMARY OF THE DISCLOSURE

Accordingly, the present disclosure is directed to a fluid drainage catheter comprising a catheter tube having proximal and distal ends and a cylindrical wall with a lumen extending generally from the proximal to the distal end to permit the passage of fluid therethrough. The catheter tube is formed such that the proximal end has a closed tip for insertion of the catheter tube into a body cavity and the distal end has an opening for the drainage of fluid from the body cavity through the catheter tube. The cylindrical wall has an outer surface with at least one defined external flow path extending generally in a longitudinal direction from a point in proximity to the closed tip to a point distally thereof. With this arrangement, at least one drainage eye is associated with the defined external flow path and extends completely through the catheter tube from the outer surface to the lumen to permit fluid in the flow path to pass through the drainage eye into the lumen.

In one particular application, the present disclosure is directed to a urinary catheter wherein the closed tip is adapted for insertion of the catheter tube into the urethra for the drainage of urine from the bladder through the lumen of the catheter tube.

In an exemplary embodiment of a urinary catheter, the cylindrical wall of the catheter tube is preferably of substantially uniform diameter from a point near the closed tip along at least the portion of the catheter tube to be inserted into the urethra. Each of the drainage eyes is advantageously positioned generally in the flow path, and advantageously at the end of the flow path located distally of the closed tip. Furthermore, the closed tip at the proximal end of the catheter tube is preferably generally rounded and a funnel is advantageously associated with the distal end of the catheter tube to define the opening for the drainage of urine.

In one embodiment, the outer surface of the cylindrical wall is formed to include at least one recessed area whereby the defined external flow path will comprise a channel extending from a point in proximity to the closed tip to one or more recessed drainage eyes. Thus, it will be understood that the outer surface of the cylindrical wall also may have two or more recessed areas defining a corresponding number of external flow channels. Preferably, the flow channels which are defined by the recessed areas in the cylindrical wall each extend generally in a longitudinal direction from a point in proximity to the closed tip in substantially uniformly spaced relation about the outer surface of the catheter tube.

An exemplary embodiment of an intermittent urinary catheter comprises a catheter tube having proximal and distal ends and a cylindrical wall with a lumen extending generally from the proximal to the distal end to permit the passage of urine therethrough. The catheter tube is formed such that the proximal end has a closed tip for insertion of the catheter tube into the urethra and the distal end has an opening for the drainage of urine from the catheter tube. The cylindrical wall has an outer surface with at least one recess defining an external flow channel extending generally in a longitudinal direction from a point in proximity to the closed tip to at least one drainage eye. The outer surface of the cylindrical wall is formed to have a substantially uniform diameter from a point near the closed tip along at least the portion of the catheter tube to be inserted into the urethra. Each of the drainage eyes is positioned generally at the end of the flow channel located distally of the closed tip so as to be in recessed relation relative to the cylindrical wall of the catheter tube. With this arrangement, each of the drainage eyes extends completely through the catheter tube from the outer surface to the lumen to permit urine in the flow channel to pass through the drainage eye into the lumen.

An exemplary embodiment of a Foley catheter comprises a catheter tube having a proximal and a distal end and a cylindrical wall with a lumen extending generally from the proximal to the distal end to permit the passage of urine therethrough. The catheter tube is formed such that the proximal end has a closed tip for insertion of the catheter tube into the urethra and the distal end has an opening for the drainage of urine from the catheter tube. The cylindrical wall has an outer surface with at least one defined external flow path extending generally longitudinally from a point in proximity to the closed tip to at least one drainage eye. The outer surface of the cylindrical wall is formed to have a substantially uniform diameter from a point near the closed tip along at least the portion of the catheter to be inserted into the urethra. The catheter tube has an inflatable balloon extending about the outer surface of the cylindrical wall so as to surround the flow path generally nearer the end thereof located distally of the closed tip. Each of the drainage eyes is positioned generally at the end of the flow path located distally of the inflatable balloon and extends completely through the catheter tube from the outer surface to the lumen to permit urine in the flow path to pass through the drainage eye into the lumen.

Other objects, features and advantages of the present disclosure will become apparent from a consideration of the following specification taken in conjunction with the accompanying drawings.

DETAILED DESCRIPTION OF THE PRESENT DISCLOSURE

Figure 1:
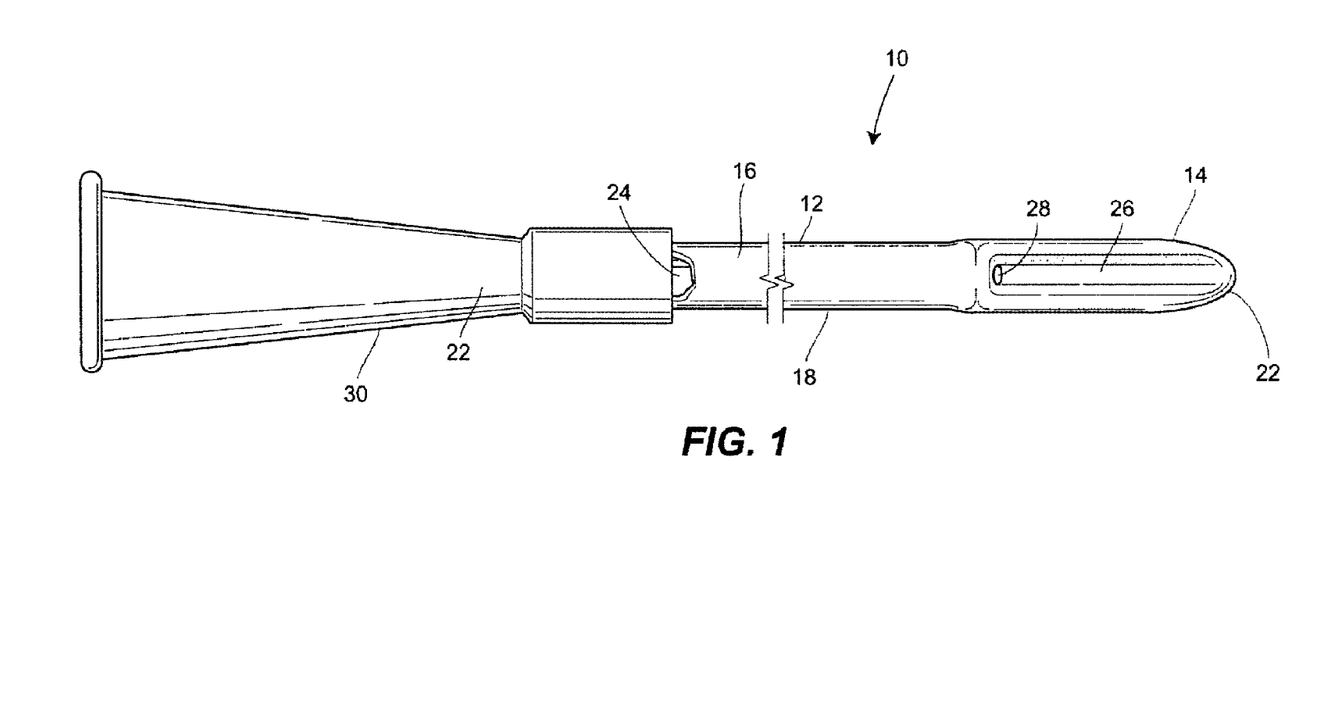
FIG. 1 is a plan view of an intermittent catheter having defined external flow paths in accordance with the present disclosure.
Figure 1A:
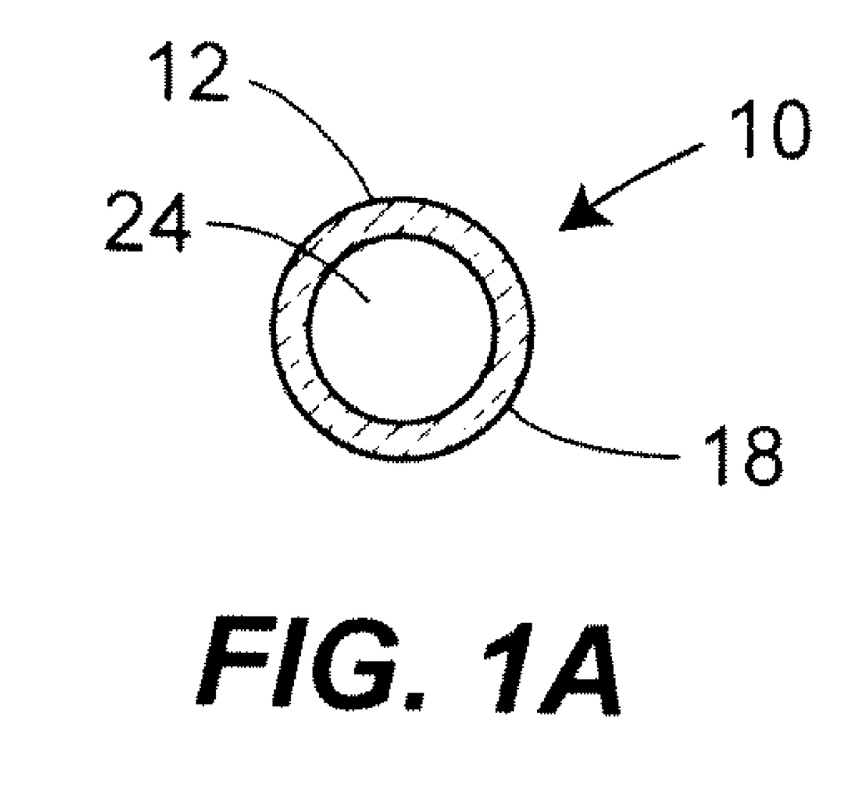
FIG. 1A is a cross-sectional view of the intermittent catheter taken along the line 1A-1A of FIG. 1.
Figure 2:
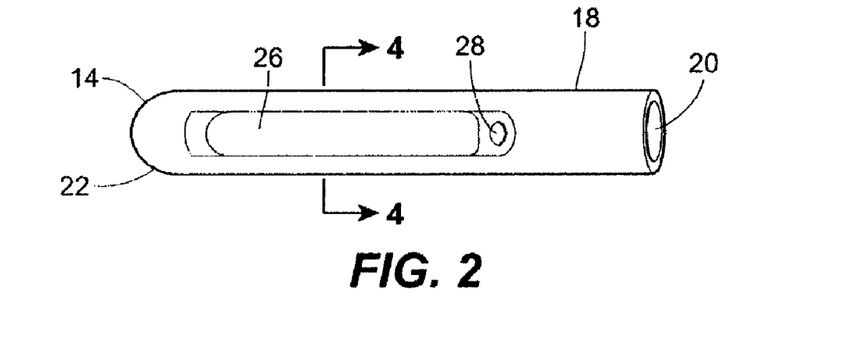
FIG. 2 is a plan view of the proximal end of the intermittent catheter of FIG. 1 illustrating a defined external flow path and drainage eye.

In the illustrations given, and with reference first to FIG. 1, the reference numeral 10 designates generally a catheter in accordance with the present disclosure. The catheter 10 comprises a catheter tube 12 having a proximal end 14 and a distal end 16 and having a cylindrical wall 18 with a lumen 20 (see FIG. 3) extending generally from the proximal end 14 to the distal end 16 to permit the passage of fluid therethrough. As shown in FIGS. 1 and 1A, the catheter tube 12 is formed such that the proximal end 14 has a closed tip 22 for insertion of the catheter tube into a body cavity and the distal end 16 has an opening as at 24 for the drainage of fluid from the body cavity through the lumen of the catheter tube 12.

Figure 3:
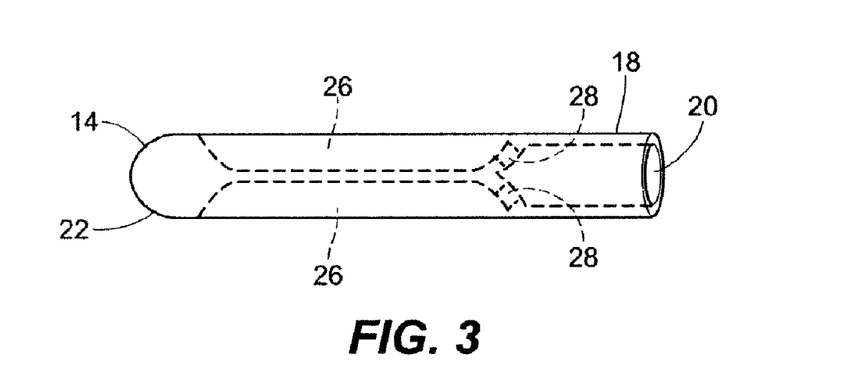
FIG. 3 is a side elevational view of the proximal end of the intermittent catheter of FIG. 2.
Figure 4:
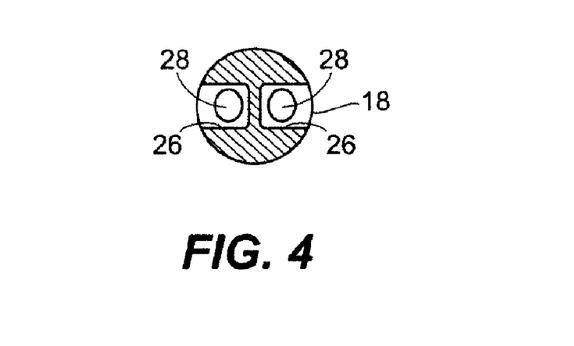
FIG. 4 is a cross-sectional view of the intermittent catheter taken along the line 4-4 of FIG. 2.

Referring to FIGS. 1-5, the cylindrical wall 18 will be seen to have an outer surface with at least one defined external flow path 26 extending generally in a longitudinal direction from a point in proximity to the closed tip 22 to a point distally thereof. As used herein, the term "defined external flow path" will be understood to mean a path which is specifically intended to accommodate the passage of fluid from one point to another as a result of structure associated with the catheter. Referring specifically to FIG. 3, at least one drainage eye 28 is associated with the defined external flow path 26 and extends completely through the catheter tube 12 from the outer surface to the lumen 20 to permit fluid in the flow path 26 to pass through the drainage eye 28 into the lumen 20.

As illustrated in FIGS. 1-5, the catheter 10 is well suited as an intermittent urinary catheter wherein the cylindrical wall 18 of the catheter tube 12 is formed to have a substantially uniform diameter from a point near the closed tip 22 along at least the portion of the catheter tube 12 to be inserted into the urethra (see FIGS. 1-4). As will also be seen from FIGS. 1-5, each of the drainage eyes 28 is positioned generally at the end of the flow path 26 which in this embodiment is defined by a recessed area in the cylindrical wall 18 which is located distally of the closed tip 22 so the flow path 26 is recessed relative to the cylindrical wall of the catheter tube 12.

While each of the drainage eyes 28 is shown generally at the end of the flow path 26 in the embodiment illustrated in FIGS. 1-5, it will be understood that the drainage eyes 28 could alternatively be positioned at any point along the recessed area in the cylindrical wall 18 defining the flow path 26.

Referring to FIG. 1, the closed tip 22 at the proximal end 14 of the catheter tube 12 is generally rounded and a funnel 30 is associated with the distal end 16 of the catheter tube 12 in communication with the opening 24 for the drainage of urine. It will also be appreciated from FIGS. 3 and 4 that the outer surface of the cylindrical wall 18 in this embodiment is preferably formed to include at least two recessed areas each defining a separate external flow path 26 in the form of a channel extending from a point in proximity to the closed tip 22 to a drainage eye 28. As shown in FIG. 3, the flow channels 26 each extend generally in a longitudinal direction from a point in proximity to the closed tip 22 in substantially uniformly spaced relation about the outer surface of the catheter tube 12 (see, also, FIG. 4).

With regard to FIG. 3, it will be seen that the flow channels are shown as extending linearly but they need not do so in order to offer the advantages of the present disclosure, e.g., the flow channels could take the form of a helix or any other form provided they extend generally in a longitudinal direction from a point in proximity to the closed tip 22.

With the intermittent catheter 10, the flow channels 26 and the drainage eyes 28 enable complete bladder drainage or at least minimize retention of residual urine in the bladder by incorporating the flow channels near the closed tip 22 so the drainage eyes 28 will permit urine in the flow channels 26 to pass into the lumen 20. By inserting the intermittent catheter 10 into the urethra until urine flow begins, the flow channels 26 will be appropriately positioned in the bladder with the drainage eyes 28 within the urethra or at the bladder neck but recessed within the flow channels 26 where they will not be blocked by the soft tissue of the bladder (see FIG. 5).

Figure 5:
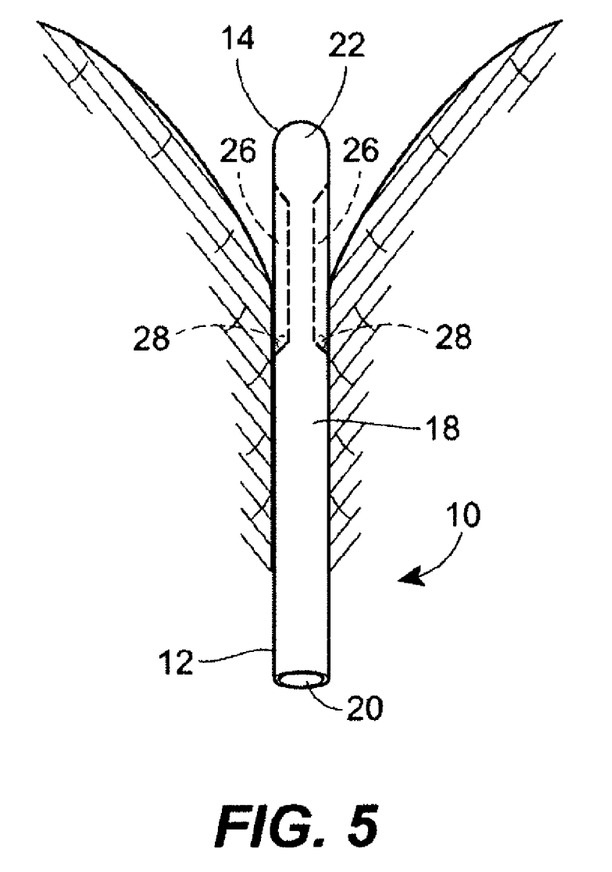
FIG. 5 is a diagrammatic view of the intermittent catheter in position within the bladder.

In other words, the proximal ends of the flow channels 26 will be suitably positioned within the bladder so urine can flow along the flow channels 26 to the drainage eyes 28 even though the drainage eyes 28 are positioned within the urethra and, since the drainage eyes 28 are recessed within the flow channels 26, they permit urine in the flow channels 26 to pass through the catheter tube 12 into the lumen 20 without precisely positioning the catheter or worrying about soft tissue blockage of the drainage eyes 28.

Figure 6:
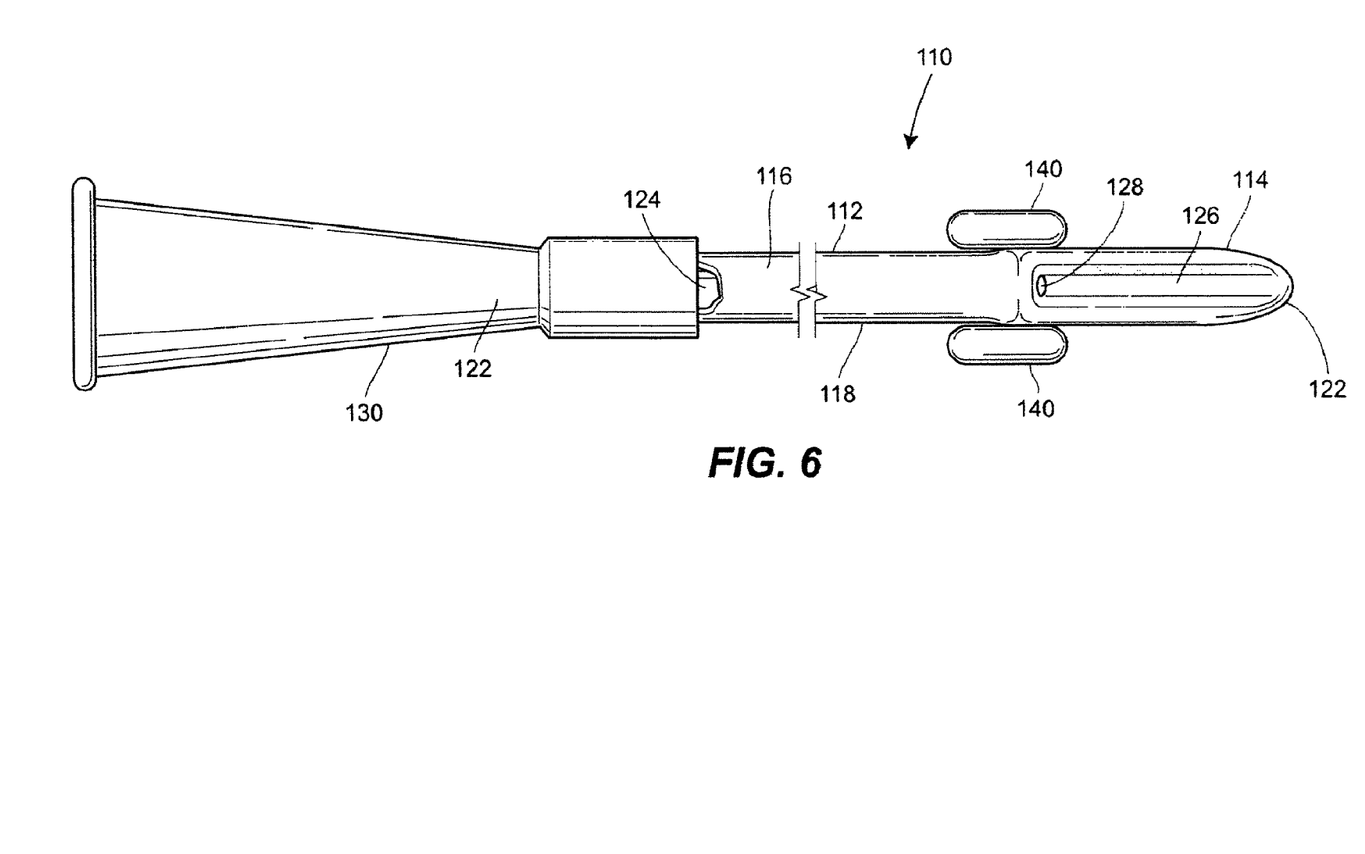
FIG. 6 is a plan view of a Foley catheter having defined external flow paths in accordance with the present disclosure.

Referring to FIG. 6, a Foley catheter 110 comprises a catheter tube 112 having a proximal end 114 and a distal end 116 and having a cylindrical wall 118 with a lumen 120 extending generally from the proximal end 114 to the distal end 116 to permit the passage of urine therethrough. The catheter tube 112 is formed such that the proximal end 114 has a closed tip 122 for insertion of the catheter tube 112 into the urethra and the distal end 116 has an opening as at 124 for the drainage of urine from the catheter tube 112. Still referring to FIG. 6, the cylindrical wall 118 will be seen to have an outer surface with at least one defined external flow path 126 extending generally in a longitudinal direction from a point in proximity to the closed tip 122 to at least one drainage eye 128.

As with the urinary catheter 10, the cylindrical wall 18 of the catheter tube 112 is formed to have a substantially uniform diameter from a point near the closed tip 122 along at least the portion of the catheter tube 112 to be inserted into the urethra. Further, the Foley catheter 110 also has an inflatable balloon 140 extending about the outer surface of the cylindrical wall 118 so as to surround the flow path 126 generally nearer the end thereof located distally of the closed tip 122.

As shown in FIG. 6, each of the drainage eyes 128 is positioned generally at the end of the flow path 126 located distally of the inflatable balloon 140 so as to be in recessed relation relative to the cylindrical wall 118 of the catheter tube 112. In addition, each of the drainage eyes 128 extends completely through the catheter tube 112 from the outer surface to the lumen 120 to permit urine in the flow path 126 to pass through the drainage eye 128 into the lumen 120.

While each of the drainage eyes 128 is shown generally at the end of the flow path 126 in the embodiment illustrated in FIG. 6, it will be understood that the drainage eyes 128 could alternatively be positioned at any point along the recessed area in the cylindrical wall 118 defining the flow path 126.

As with the intermittent catheter 10, the Foley catheter 110 is formed with the closed tip 122 at the proximal end 114 of the catheter tube 112 generally rounded and a funnel 130 is associated with the distal end 116 of the catheter tube in communication with the opening 124 for the drainage of urine. Also, as with the intermittent catheter 10, the Foley catheter 110 is preferably formed to include at least one and preferably two or more recessed areas each defining a separate external flow path in the form of a channel extending from a point in proximity to the closed tip 122 to a drainage eye 128. Furthermore, the flow channels 126 each extend generally in a longitudinal direction from a point in proximity to the closed tip 122 in substantially uniformly spaced relation about the outer surface of the catheter tube 112 substantially in the manner shown in FIG. 3. Additionally, the Foley catheter 110 is formed in this embodiment such that the inflatable balloon 140 has a toroidal shape and completely encircles the catheter tube 112 when inflated to thereby encircle the flow channels 126.

With the Foley catheter 110, it is possible to lengthen the duration the catheter can be left in place in a patient prone to encrustation. Published research suggests that irregular eye surfaces are readily colonized and blocked by crystalline bacterial bio-film. With the flow channels 126 and drainage eyes 128, there is a reduced tendency of bio-films to form and encrustation to occur.

Figure 7A:
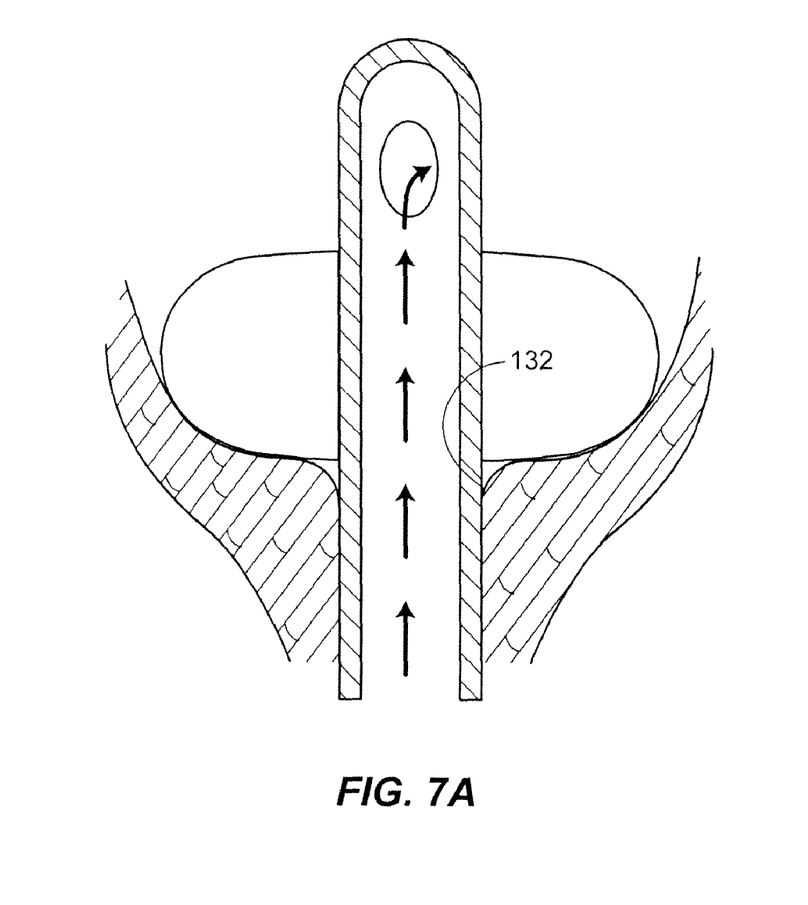
FIG. 7A is a cross-sectional view illustrating a path for bacteria through the lumen of a conventional Foley catheter and in position within the bladder.

Referring to FIG. 7A, a conventional Foley catheter is shown in position within the bladder with the balloon inflated. It will be noted that the epithelial (or surface) cell layer 132 within the urinary tract is essentially isolated from bacteria that can reach the bladder (as represented by the arrows) by passing through the lumen of the catheter and the drainage eye. Unfortunately, the inability of the bacteria to reach the epithelial cell layer 132 is detrimental to the protection of the urinary tract.

More specifically, the epithelial cells provide a natural chemical defense system because of the presence in the cells of cathelicidin which is an endogenous antibiotic. This antibiotic is present in low concentrations normally but upon bacterial attachment the epithelial cells rapidly increase the production and release of cathelicidin. Thus, epithelial cathelicidin is an important defense for protecting the urinary tract, but the passage of bacteria directly into the bladder fails to take advantage of this fact.

Figure 7B:
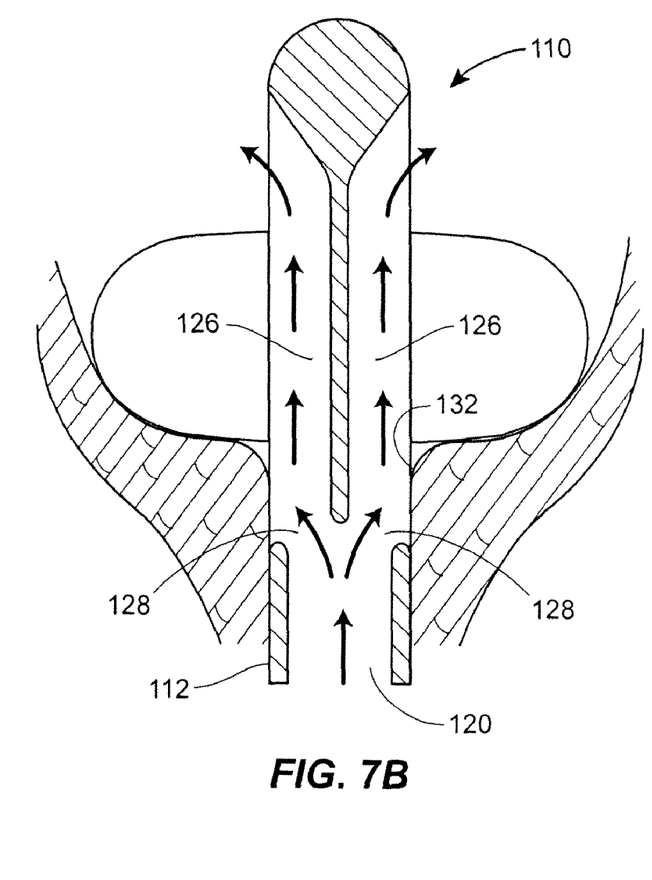
FIG. 7B is a cross-sectional view illustrating a path for bacteria through the lumen of the Foley catheter of FIG. 6 and in position within the bladder.

Referring now to FIG. 7B, the pathway for bacteria approaching the bladder (as represented by the arrows) will be seen to be in close proximity to the epithelial cell layer 132. With the Foley catheter 110 constructed in accordance with the disclosure, the bacteria passes through the lumen 120 of the catheter tube 112 and then through the drainage eyes 128 and the flow paths or channels 126 such that the bacteria easily contacts the epithelial cell layer 132. As a result, the contact of the bacteria with the epithelial cell layer 132 permits the natural chemical defense system of the epithelial cell layer to operate to thereby offer protection to the urinary tract.

Figure 8A:
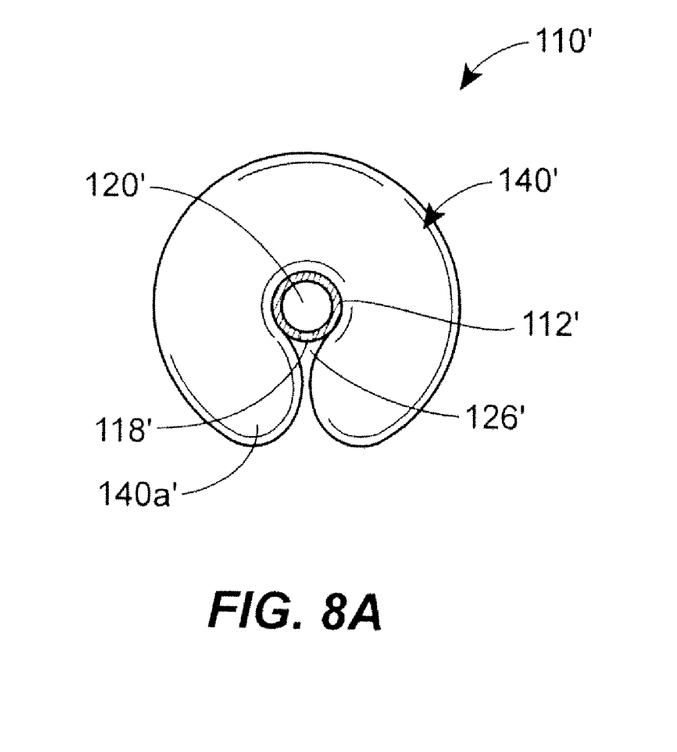
FIG. 8A is a cross-sectional view of another Foley catheter embodiment having a defined external flow path in accordance with the present disclosure.
Figure 8B:
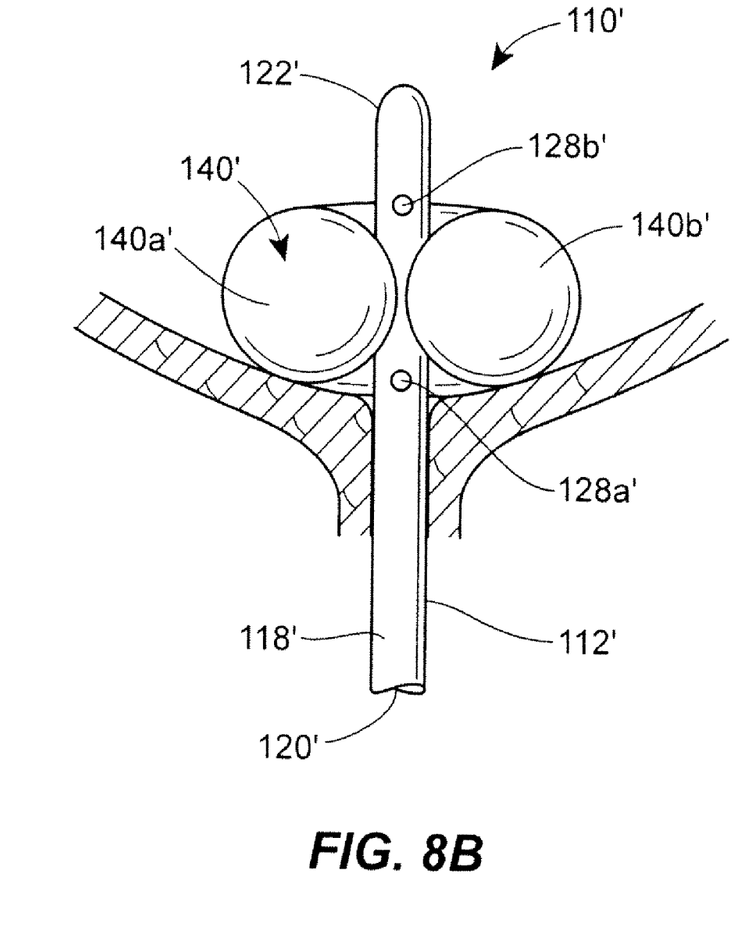
FIG. 8B is a plan view of the Foley catheter of FIG. 8A illustrating the defined external flow path with the catheter in position within the bladder.

Referring to FIGS. 8A and 8B, another embodiment of Foley catheter 110' comprises a catheter tube 112' having a proximal end and a distal end and having a cylindrical wall 118' with a lumen 120' extending generally from the proximal end to the distal end. It is similar in many respects to the Foley catheter 110, but it also differs in that the catheter tube 112' has an inflatable balloon 140' extending substantially, but less than entirely, about the outer surface of the cylindrical wall 118' and has adjacent lobes 140a' and 140b' spaced from the outer surface of the cylindrical wall 118' to define the external flow path 126' as the space between the outer surface of the cylindrical wall 118' and the adjacent lobes 140a' and 140b'. In addition, the drainage eye 128a' extends completely through the catheter tube 112' generally at the end of the defined external flow path 126' located distally of the inflatable balloon 140' to permit urine in the flow path to pass through the drainage eye into the lumen.

With the embodiment illustrated in FIGS. 8A and 8B, the balloon 140' can be provided with varying wall thickness to achieve the desired inflated shape such as shown in the drawings. The balloon 140' is interrupted, i.e., it does not wrap the full 360 degrees around the catheter tube 112', to thereby provide the defined external flow path 126' as a result of the prominence of the adjacent lobes 140a' and 140b' which can be controlled by adjusting the wall thickness. By making the balloon wall thicker in the region of the lobes 140a' and 140b', the majority of the balloon having a thinner wall reaches its strain limit while the thicker walls will continue to expand.

Because the thicker walls of the lobes 140a' and 140b' continue to expand relative to the majority of the balloon, it is possible to form the lobes in the illustrated shape through inflation which, in turn, forms the defined external flow path 126'.

If desired, the Foley catheter 110' can also have a drainage opening as at 128b' located distally of the closed tip 122' but proximally of the balloon 140'.

Figure 9A:
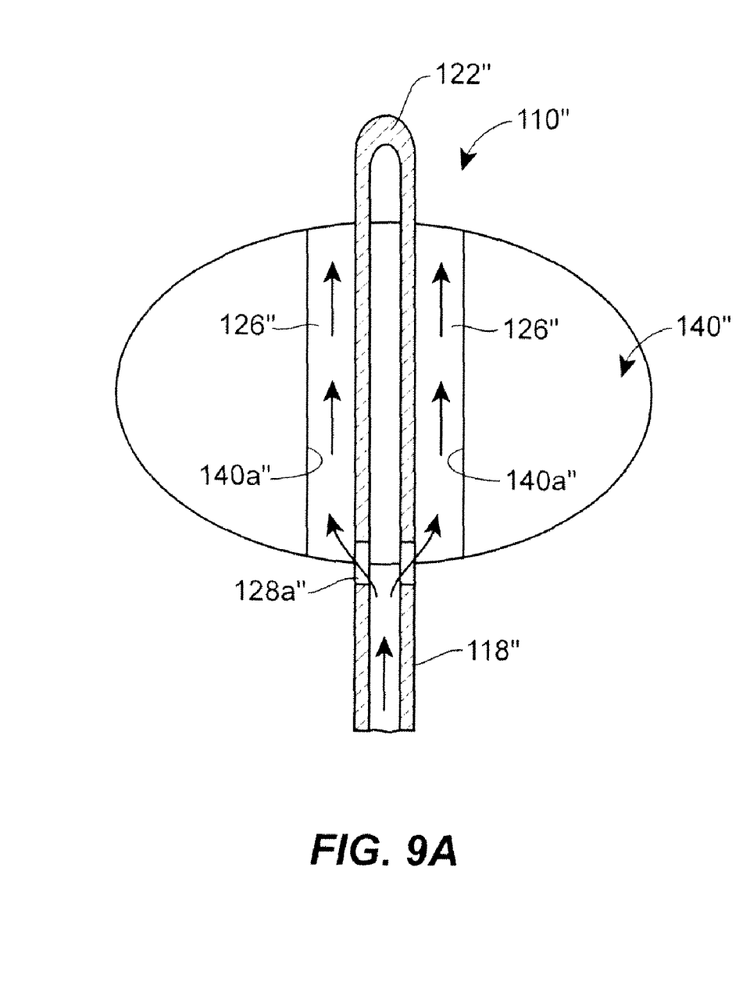
FIG. 9A is a cross-sectional view of another Foley catheter embodiment having defined external flow paths in accordance with the present disclosure.
Figure 9B:
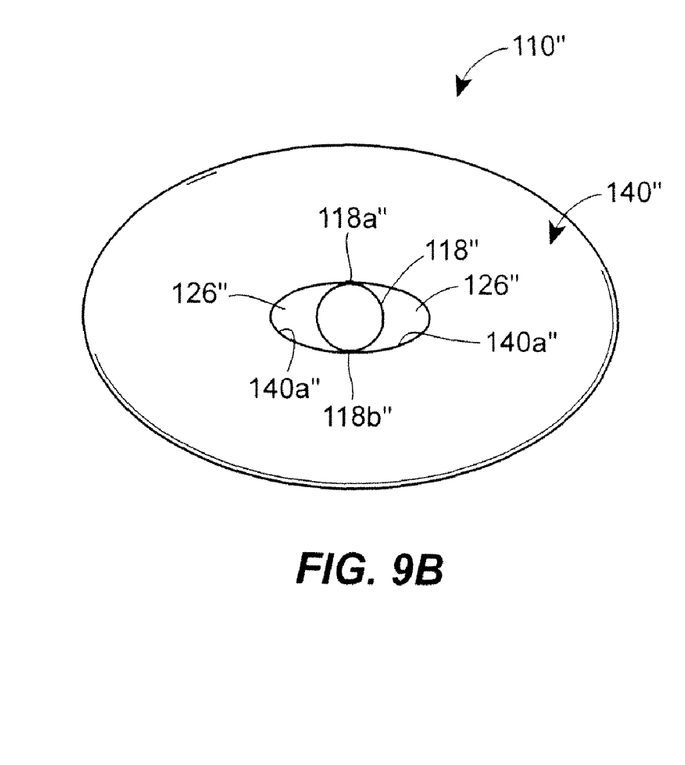
FIG. 9B is a plan view of the Foley catheter of FIG. 9A illustrating the defined external flow paths in relation to the catheter and the balloon.

As a further alternative (see FIGS. 9A and 9B), the Foley catheter such as 110" can include a balloon such as 140" which extends continuously and completely about the outer surface of the cylindrical wall 118". The balloon 140" can be attached to the outer surface of the cylindrical wall 118" at one or more locations such as 118a" and 118b" as best illustrated in FIG. 9B, but the balloon can otherwise be spaced from the outer surface of the cylindrical wall 118" when inflated to define flow paths such as 126". While shown forming two external flow paths 126" as the result of two attachment points, it will be appreciated that the balloon 140" can be attached in such a way as to form one, two or more such flow paths.

In particular, the flow paths such as 126" will be defined by the space (or spaces) between the cylindrical wall 118" where the balloon 140" is not attached and the inwardly facing wall (or walls) 140a" of the balloon 140" when inflated.

As a still further alternative (see FIGS. 10, 10A and 10B), the Foley catheter such as 110''' can include a multi-lobed balloon such as 140''' wherein the lobed balloon extends substantially about the outer surface of the cylindrical wall 118'''. The balloon generally designated 140''' in FIG. 10 comprises a single balloon having two or more integral balloon segments, but it can comprise two, three or more separate balloons although, in either case, the balloon(s) can be formed to have two pairs of adjacent lobes 140a''' and 140b''' as illustrated in FIG. 10A, three pairs of adjacent lobes 140a''' and 140b''' as illustrated in FIG. 10B, etc. If the balloon comprises separate balloons, they can be attached to the outer surface of the cylindrical wall 118"' at two locations 118a''' and 118b''' (FIG. 10A), three locations such as 118a''', 118b''' and 118c''' (FIG. 10B), etc.

Figure 10:
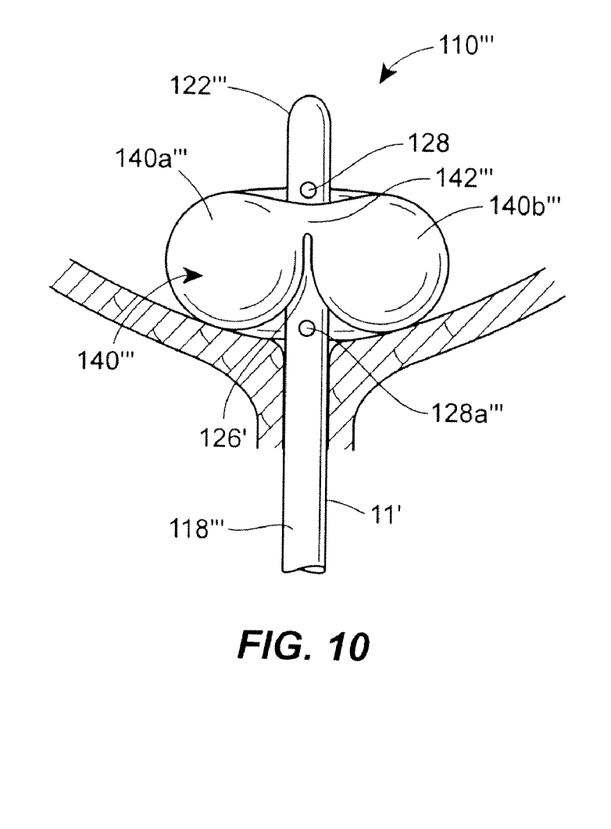
FIG. 10 is a diagrammatic view of another Foley catheter embodiment having a multi-lobed balloon in position within the bladder.
Figure 10A:
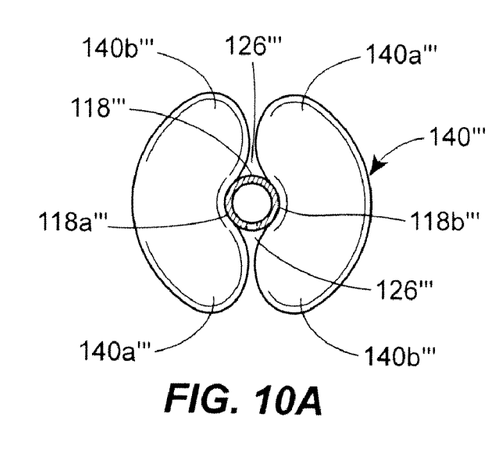
FIG. 10A is a cross-sectional view of the Foley catheter of FIG. 10 illustrating a two-lobed balloon version.
Figure 10B:
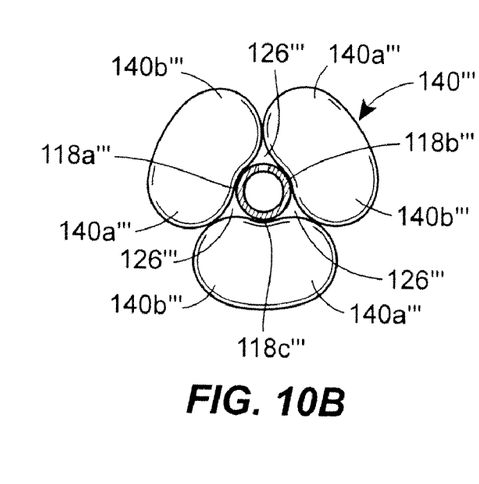
FIG. 10B is a cross-sectional view of the Foley catheter of FIG. 10 illustrating a three-lobed balloon version.

While the balloon 140''' can be formed of separate balloons, it can have continuous region 142''' to define a balloon "header" or "manifold" when it is formed as a single balloon having two or more integral balloon segments as shown in FIG. 10). The balloon 140''' still can be attached to the outer surface of the cylindrical wall 118''' in two or more places depending upon the number of pairs of adjacent lobes being utilized to form the desired number of external flow paths 126'''. By providing the continuous region 142''', there will be a continuous balloon structure encircling the cylindrical wall 118''' which can be advantageous for uniformly inflating the balloon 140''' and creating uniform external flow paths 126'''.

With an embodiment utilizing balloons to define or form external flow paths in cooperation with the outer surface of the cylindrical wall of a Foley catheter, a drainage eye such as 128a' (FIG. 8B) or 128a" (FIG. 9A) or 128a''' (FIG. 10) will be positioned generally at the end of one or more of the respective defined external flow paths 126', 126" and 126''' so as to be located distally of the respective closed tips 122', 122" and 122''' and the respective balloons 140', 140" and 140'''.

Both intermittent and Foley-type urinary catheters have been described in detail for purposes of understanding the present disclosure, but it will be understood that the catheter structure described herein has wide ranging applicability as a fluid drainage catheter for draining fluid from any body cavity.

While the foregoing sets forth a detailed description of the preferred disclosure, it will be appreciated by those skilled in the art that the details herein given may be varied without departing from the true spirit and scope of the disclosure as set forth in the appended claims.

What is claimed is:

1. A catheter for the drainage of urine from a bladder, comprising:

a catheter tube having a proximal end and a distal end and having a cylindrical wall with a lumen extending generally from the proximal end to the distal end to permit the passage of urine therethrough;

the catheter tube being formed such that the proximal end thereof has a closed tip for insertion of the catheter tube through a urethra until the closed tip is positioned in the bladder and the distal end thereof has an opening for the drainage of urine from the bladder through the lumen of the catheter tube;

the cylindrical wall having an outer surface with at least one defined external flow path extending generally in a longitudinal direction from a point to be positioned in the bladder in proximity to the closed tip to a point to be positioned in the urethra distally thereof; and at least one drainage eye associated with the defined external flow path when the point of the external flow path in proximity to the closed tip is positioned within the bladder, the drainage eye extending completely through the catheter tube from the outer surface to the lumen to permit urine in the flow path to pass through the drainage eye into the lumen.

2. The catheter of claim 1 wherein the cylindrical wall of the catheter tube is of substantially uniform diameter from a point near the closed tip along at least a portion of the catheter tube to be inserted into the urethra.

3. The catheter of claim 1 wherein the drainage eye is positioned generally at the end of the external flow path located distally of the closed tip to permit urine in the flow path to pass through the catheter tube.

4. The catheter of claim 1 wherein the closed tip at the proximal end of the catheter tube is generally rounded and including a funnel associated with the distal end of the catheter tube defining the opening for the drainage of urine.

5. The catheter of claim 1 wherein the outer surface of the cylindrical wall has at least one recessed area whereby the external flow path comprises a channel defined by the recessed area and extending from a point in proximity to the closed tip to a point distally thereof.

6. The urinary catheter of claim 5 including at least two channels each extending generally in a longitudinal direction from a point in proximity to the closed tip in substantially uniformly spaced relation about the outer surface of the catheter tube.

7. A urinary catheter for the drainage of urine from a bladder, comprising:

a catheter tube having a proximal end and a distal end and having a cylindrical wall with a lumen extending generally from the proximal end to the distal end to permit the passage of urine therethrough;

the catheter tube being formed such that the proximal end thereof has a closed tip for insertion of the catheter tube through a urethra until the closed tip is positioned in the bladder and the distal end thereof has an opening for the drainage of urine from the bladder through the lumen of the catheter tube;

the cylindrical wall having an outer surface with at least one recessed area defining an external flow channel extending generally in a longitudinal direction from a point to be positioned in the bladder in proximity to the closed tip to a point to be positioned in the urethra distally thereof; and at least one drainage eye associated with the external flow channel so the drainage eye will be positioned in the urethra or at a neck of the bladder when the point of the external flow channel in proximity to the closed tip is positioned within the bladder, the drainage eye extending completely through the catheter tube from the outer surface to the lumen to permit urine in the flow channel to pass through the drainage eye into the lumen.

8. The urinary catheter of claim 7 wherein the cylindrical wall of the catheter tube is of substantially uniform diameter from a point near the closed tip along at least a portion of the catheter tube to be inserted into the urethra.

9. The urinary catheter of claim 7 wherein the drainage eye is positioned generally at the end of the external flow channel located distally of the closed tip to be in recessed relation relative to the cylindrical wall of the catheter tube.

10. The urinary catheter of claim 7 wherein the closed tip at the proximal end of the catheter tube is generally rounded and including a funnel associated with the distal end of the catheter tube defining the opening for the drainage of urine.

11. The urinary catheter of claim 7 wherein the outer surface of the cylindrical wall has at least two recessed areas each defining a separate external flow channel extending from a point in proximity to the closed tip to at least one drainage eye.

12. The urinary catheter of claim 11 wherein the flow channels each extend generally in a longitudinal direction from a point in proximity to the closed tip in substantially uniformly spaced relation about the outer surface of the catheter tube.

13. An intermittent urinary catheter for the drainage of urine from a bladder, comprising:

a catheter tube having a proximal end and a distal end and having a cylindrical wall with a lumen extending generally from the proximal end to the distal end to permit the passage of urine therethrough;

the catheter tube being formed such that the proximal end thereof has a closed tip for insertion of the catheter tube through a urethra until the closed tip is positioned in the bladder and the distal end thereof has an opening for the drainage of urine from the bladder through the lumen of the catheter tube;

the cylindrical wall having an outer surface with at least one recessed area defining an external flow channel extending generally in a longitudinal direction from a point to be positioned in the bladder in proximity to the closed tip to at least one drainage eye;

the outer surface of the cylindrical wall being formed to have a substantially uniform diameter from a point near the closed tip along at least a portion of the catheter tube to be inserted into the urethra;

the drainage eye being positioned generally at the end of the flow channel located distally of the closed tip so as to be in recessed relation relative to the cylindrical wall of the catheter tube and positioned in the urethra or at a neck of the bladder when the point of the flow channel in proximity to the closed tip is positioned within the bladder;

the drainage eye extending completely through the catheter tube from the outer surface to the lumen to permit urine in the flow channel to pass through the drainage eye into the lumen.

14. The urinary catheter of claim 13 wherein the closed tip at the proximal end of the catheter tube is generally rounded and including a funnel associated with the distal end of the catheter tube defining the opening for the drainage of urine.

15. The urinary catheter of claim 14 wherein the outer surface of the cylindrical wall has at least two recessed areas each defining a separate external flow channel extending from a point in proximity to the closed tip to at least one drainage eye.

16. The urinary catheter of claim 15 wherein the flow channels each extend generally in a longitudinal direction from a point in proximity to the closed tip in substantially uniformly spaced relation about the outer surface of the catheter tube.

17. A catheter, comprising:

a catheter tube having a proximal end and a distal end and having a cylindrical wall with a lumen extending generally from the proximal end to the distal end to permit the passage of urine therethrough;

the catheter tube being formed such that the proximal end thereof has a closed tip for insertion of the catheter tube into the urethra and the distal end thereof has an opening for the drainage of urine from the catheter tube;

the cylindrical wall having an outer surface with at least one defined external flow path extending generally in a longitudinal direction from a point in proximity to the closed tip to at least one drainage eye;

the outer surface of the cylindrical wall being formed to have a substantially uniform diameter from a point near the closed tip along at least the portion of the catheter tube to be inserted into the urethra;

the catheter tube having an inflatable balloon extending at least substantially about the outer surface of the cylindrical wall to surround the defined external flow path generally nearer the end thereof located distally of the closed tip;

each of the drainage eyes being positioned generally at the end of the defined external flow path located distally of the inflatable balloon and extending completely through the catheter tube from the outer surface to the lumen to permit urine in the flow path to pass through the drainage eye into the lumen.

18. The catheter of claim 17 wherein the closed tip at the proximal end of the catheter tube is generally rounded and including a funnel associated with the distal end of the catheter tube defining the opening for the drainage of urine.

19. The catheter of claim 18 wherein the outer surface of the catheter tube is formed to include at least one recessed area whereby the external flow path comprises a channel defined by the recessed area and extending from a point in proximity to the closed tip to at least one drainage eye.

20. The catheter of claim 19 including at least two flow channels each extending generally in a longitudinal direction from a point in proximity to the closed tip in substantially uniformly spaced relation about the outer surface of the catheter tube.

21. The catheter of claim 20 wherein the inflatable balloon completely encircles the catheter tube when inflated to thereby completely encircle the flow channels to secure the catheter tube in position within the bladder for the drainage of urine therefrom.

22. The catheter of claim 17 wherein the balloon when inflated secures the catheter tube such that the drainage eye is in proximity to the epithelial cells for exposure to bacteria passing through the lumen from the proximal to the distal end of the catheter tube.

23. A catheter, comprising:

a catheter tube having a proximal end and a distal end and having a cylindrical wall with a lumen extending generally from the proximal end to the distal end to permit the passage of urine therethrough;

the catheter tube being formed such that the proximal end thereof has a closed tip for insertion of the catheter tube into the urethra and the distal end thereof has an opening for the drainage of urine from the catheter tube;

the cylindrical wall having an outer surface with at least one defined external flow path extending generally in a longitudinal direction from a point in proximity to the closed tip to a drainage eye located distally thereof;

the outer surface of the cylindrical wall being formed to have a substantially uniform diameter from a point near the closed tip along at least the portion of the catheter tube to be inserted into the urethra;

the catheter tube having an inflatable balloon extending less than entirely about the outer surface of the cylindrical wall and having adjacent lobes spaced from the outer surface of the cylindrical wall to define the external flow path as the space between the outer surface of the cylindrical wall and the adjacent lobes;

the drainage eye being positioned generally at the end of the defined external flow path located distally of the inflatable balloon and extending completely through the catheter tube from the outer surface to the lumen to permit urine in the flow path to pass through the drainage eye into the lumen.

24. The catheter of claim 23 including at least a pair of balloons together extending at least substantially about the outer surface of the cylindrical wall and together having pairs of adjacent lobes spaced from the outer surface of the cylindrical wall such that each of the pairs of adjacent lobes forms an external flow path in the space between the outer surface of the cylindrical wall and the adjacent lobes and including a drainage eye positioned generally at the end of at least one of the defined external flow paths.

25. The catheter of claim 23 including a balloon having a continuous region attached to the outer surface of the cylindrical wall in at least two places and having two or more pairs of adjacent lobes spaced from the outer surface of the cylindrical wall in locations where the continuous region is not attached such that each of the pairs of adjacent lobes forms an external flow path in the space between the outer surface of the cylindrical wall and the adjacent lobes and including a drainage eye positioned generally at the end of at least one of the defined external flow paths.

26. The catheter of claim 23 including two or more separate balloons together extending entirely about the outer surface of the cylindrical wall and having two or more pairs of adjacent lobes spaced from the outer surface of the cylindrical wall to define two or more external flow paths as the space between the outer surface of the cylindrical wall and the pairs of adjacent lobes.

* * * * *